US007846091B2

(12) United States Patent
Fulghum

(10) Patent No.: US 7,846,091 B2
(45) Date of Patent: Dec. 7, 2010

(54) AUTOFLUORESCENCE IMAGING SYSTEM FOR ENDOSCOPY

(75) Inventor: Stephen F. Fulghum, Marblehead, MA (US)

(73) Assignee: Newton Laboratories, Inc., Woburn, MA (US)

(*) Notice: Subject to any disclaimer, the term of this patent is extended or adjusted under 35 U.S.C. 154(b) by 0 days.

(21) Appl. No.: 10/092,033

(22) Filed: Mar. 5, 2002

(65) Prior Publication Data

US 2002/0161282 A1 Oct. 31, 2002

Related U.S. Application Data

(63) Continuation of application No. 09/362,806, filed on Jul. 28, 1999, now Pat. No. 6,364,829, which is a continuation-in-part of application No. 09/238,664, filed on Jan. 26, 1999, now Pat. No. 6,537,211.

(51) Int. Cl.
  *A61B 1/06* (2006.01)
  *A61B 6/00* (2006.01)
(52) U.S. Cl. .................. 600/160; 600/178; 600/476
(58) Field of Classification Search ................. 600/160, 600/109, 178, 182, 476, 477, 478; 250/458.1, 250/484.2, 461.2
  See application file for complete search history.

(56) References Cited

U.S. PATENT DOCUMENTS

| | | | |
|---|---|---|---|
| 4,253,447 A | 3/1981 | Moore et al. | |
| 4,261,344 A | 4/1981 | Moore et al. | |
| 4,449,535 A | 5/1984 | Renault | |
| 4,604,992 A | 8/1986 | Sato | |
| 4,746,203 A | 5/1988 | Nishioka et al. | |
| 4,821,117 A | 4/1989 | Sekiguchi | |
| 4,846,155 A | 7/1989 | Kimura | |

(Continued)

FOREIGN PATENT DOCUMENTS

DE    195 35 114 A1    3/1996

(Continued)

OTHER PUBLICATIONS

"IV6C5-20/35," Olympus Industrial Endoscope Products, pp. 1-2, downloaded Apr. 24, 1996 from http://www.infoweb....e/iv6c5-2030E.html.

(Continued)

*Primary Examiner*—John P Leubecker
(74) *Attorney, Agent, or Firm*—Weingarten, Schurgin, Gagnebin & Lebovici LLP

(57) ABSTRACT

A system and method for imaging tissue autofluorescence through a video endoscope is described, comprising a light source capable of providing both ultraviolet light capable of inducing tissue autofluorescence and visible light which induces little or no autofluorescence, an optical system to deliver both wavelength bands to the tissue with the same apparent spatial and angular intensity distribution, a means for digitally acquiring the resulting, visible fluorescence and visible reflectance images using a single imaging detector at the distal tip of the endoscope and a means for digitally processing said images to generate a final, false-color image for display which indicates regions of tissue dysplasia. This system can either be added on to an existing video endoscope or integrated into its structure. The combined system can be electronically switched between normal white light imaging and fluorescence imaging.

32 Claims, 12 Drawing Sheets

U.S. PATENT DOCUMENTS

| | | | |
|---|---|---|---|
| 4,852,579 | A | 8/1989 | Gilstad et al. |
| 4,860,095 | A | 8/1989 | Kimura et al. |
| 5,058,568 | A | 10/1991 | Irion et al. |
| 5,187,572 | A | 2/1993 | Nakamura et al. |
| 5,228,438 | A | 7/1993 | Sakamoto |
| 5,241,170 | A | 8/1993 | Field, Jr. et al. |
| 5,247,533 | A * | 9/1993 | Okazaki et al. ............... 372/45 |
| 5,255,087 | A | 10/1993 | Nakamura et al. |
| 5,298,741 | A | 3/1994 | Walt et al. |
| 5,305,098 | A | 4/1994 | Matsunaka et al. |
| 5,363,854 | A | 11/1994 | Martens et al. |
| 5,381,784 | A | 1/1995 | Adair |
| 5,396,329 | A | 3/1995 | Kalawsky |
| 5,413,108 | A | 5/1995 | Alfano |
| 5,421,339 | A | 6/1995 | Ramanujam et al. |
| 5,438,975 | A | 8/1995 | Miyagi et al. |
| 5,452,723 | A | 9/1995 | Wu et al. |
| 5,494,483 | A | 2/1996 | Adair |
| 5,647,368 | A | 7/1997 | Zeng et al. |
| 5,701,903 | A | 12/1997 | Sano et al. |
| 5,719,399 | A | 2/1998 | Alfano et al. |
| 5,749,830 | A | 5/1998 | Kaneko et al. |
| 5,769,792 | A | 6/1998 | Palcic et al. |
| 5,772,580 | A | 6/1998 | Utsui et al. |
| 5,827,190 | A | 10/1998 | Palcic et al. |
| 5,840,017 | A | 11/1998 | Furusawa et al. |
| 5,847,394 | A | 12/1998 | Alfano et al. |
| 5,891,016 | A | 4/1999 | Utsui et al. |
| 5,979,423 | A * | 11/1999 | Poindexter et al. .......... 123/697 |
| 5,989,181 | A | 11/1999 | Dutting et al. |
| 5,999,844 | A | 12/1999 | Gombrich et al. |
| 6,061,591 | A | 5/2000 | Freitag et al. |
| 6,091,984 | A * | 7/2000 | Perelman et al. ............ 600/476 |
| 6,104,939 | A * | 8/2000 | Groner et al. ................ 600/322 |
| 6,124,597 | A | 9/2000 | Shehada et al. |
| 6,148,227 | A * | 11/2000 | Wagnieres et al. .......... 600/476 |
| 6,201,989 | B1 | 3/2001 | Whitehead et al. |
| 6,293,911 | B1 * | 9/2001 | Imaizumi et al. ............ 600/160 |
| 6,318,887 | B1 | 11/2001 | Matsumoto |
| 6,331,156 | B1 | 12/2001 | Haefele et al. |
| 6,449,006 | B1 | 9/2002 | Shipp |
| 6,730,019 | B2 | 5/2004 | Irion |
| 2002/0093563 | A1 | 7/2002 | Cline et al. |

FOREIGN PATENT DOCUMENTS

| | | |
|---|---|---|
| DE | 196 27 369 | 10/1997 |
| DE | 100 33 142 A1 | 1/2001 |
| WO | WO 89/02718 | 4/1989 |
| WO | WO 92/15008 | 9/1992 |
| WO | WO 92/19148 | 11/1992 |
| WO | WO 93/25137 | 12/1993 |
| WO | WO 94/09694 | 5/1994 |
| WO | WO 94/23539 | 10/1994 |
| WO | WO 95/11624 | 5/1995 |
| WO | WO 95/26674 | 10/1995 |
| WO | WO 99/188847 | 4/1999 |
| WO | WO 99/53832 | 10/1999 |
| WO | WO 99/65394 | 12/1999 |
| WO | WO 00/06980 | 2/2000 |
| WO | WO 00/54652 | 9/2000 |

OTHER PUBLICATIONS

"IK-SM40 Super Micro Camera," Toshiba Review (f02index.htm '95.11.1), total of 4 pages, downloaded on Apr. 24, 1996 from http://toshiba....95/11/f02/index.htm.

Perelman. L.T., et al., "Spectroscopic diagnostics of epithelial tissues with polarized light." (From SPIE Abstract) No date given.

Wang, T. et al., "Laser-induced fluorescence endoscopic imaging for detection of colonic dysplasia." Presented at SPIE Meeting. (Feb. 4, 1995).

Wang, T., et al., "Real-time in vivo endoscopic imaging of fluorescence from human colonic adenomas." Paper presented at the meeting of the Society of Photonics Instrumentation Engineering—Systems and Technologies for Clinical Diagnostics and Drug Discovery, San Jose, CA (Jan. 1998).

Wang, T., et al., "Fluorescence Endoscopic Imaging of Human Colonic Adenomas," *Gastroenterology*, pp. 1182-1191 (1996).

Wang, T., et al., "In Vivo Identification of Colonic Dysplasia Using Fluorescence Endoscopic Imaging," *Gastrointestinal Endoscopy* pp. 1-38 (Jun. 10, 1998).

Zonios, G., et al., "Diffuse Reflectance Spectroscopy of human Adenomatous Colon Polyps In Vivo," pp. 1-30 (1998).

Wang, T., "Fluorescence Endoscopic Imaging System for Detection of Colonic Adenomas," pp. 1-187 (1996).

Wang, T., et al., "Mathematical Model of Fluorescence Endoscopic Image Formation," *Applied Optics* pp. 1-38 (1998).

Wang, T., et al., "Model of Endoscopic Image Formation with Application to Fluorescence of Biological Tissue" pp. 1-33 (1998).

Tappy, T., and Baur, C., "Systeme d'entrainement pour chirurgie endoscopique utilisant la realite virtuelle," pp. 1-5 No date given.

Han et al., "AlGaN/GaN quantum well ultraviolet light emitting diodes", Applied Physics Letters, vol. 73, No. 12, pp. 1688-1690, 1998.

\* cited by examiner

AUTOFLUORESCENCE IMAGING SYSTEM FOR ENDOSCOPY

RELATED APPLICATION

This is a continuation of U.S. application Ser. No. 09/362,806 filed on Jul. 28, 1999, now U.S. Pat. No. 6,364,829, issued Apr. 2, 2002, which is a continuation-in-part of U.S. application Ser. No. 09/238,664 filed Jan. 26, 1999, now U.S. Pat. No. 6,537,211, issued Mar. 25, 2003, the entire contents of which are incorporated herein by reference.

GOVERNMENT SUPPORT

This invention was supported in whole or in part by a grant from the National Institute of Health, Grant No. R44CA72626, "Imaging Spectrofluorimeter for Colonic Dysplasia". The Government has certain rights in the invention.

BACKGROUND OF THE INVENTION

Advanced stage cancers are difficult to treat effectively, so it is important to detect them in their premalignant stages, such as dysplasia or carcinoma in situ. Currently, the most widely used method for early detection uses visual inspection trough endoscopes, which relies upon the recognition of the gross architectural changes associated with dysplasia. Visual inspection is less effective in detecting the superficial lesions of flat dysplasia, such as ulcerative colitis and Barrett's esophagus. In these cases, surveillance requires the selection of representative sites for biopsy and subsequent histological analysis. Only a very small fraction of a large surface, such as the colon, can be surveyed in this manner and small areas of dysplasia may go undetected. More efficient methods for detecting flat dysplasia would provide a significant means of reducing cancer morbidity, mortality, and costs.

A promising technique for detecting dysplasia during endoscopy involves illuminating the tissue with light of an appropriate wavelength and observing the resulting fluorescence. Tissue fluorescence occurs at longer wavelengths than the excitation illumination and is typically much weaker, so that spectroscopic techniques are generally required for its detection. Diagnostic methods which use fluorescence information can generally be divided into two groups. The first group of methods observes fluorescence from medications administered to the patient which have accumulated in tumor tissues. The second group of methods observes endogenous fluorescence or autofluorescence arising from substances natural to the tissue itself which change their relative concentrations when the tissue becomes dysplastic. Of the two general fluorescence methods, the first method, requiring a prior application of a drug, is the more invasive. The application of these drugs takes additional time and has the potential of causing adverse side effects. Methods based on autofluorescence detection are less invasive and more suited to endoscopy for screening purposes.

Normal colon tissue, for example, when illuminated with ultraviolet light at 370 nm, exhibits a broad, blue fluorescence with a peak at 450 nm, as shown in FIG. 1. This fluorescence is due to collagen, the primary protein of connective tissue, which is found within the thin mucosal layer and which is the dominant component of the submucosal layer. The fluorescence of dysplastic colon tissue, due to changes in its structure and chemistry, is typically ½ to ⅓ as intense given the same illumination. This reduction in visible blue-green autofluorescence, produced by ultraviolet to violet excitation light, has been identified as a primary indicator of dysplastic tissue. An increase in the relative fluorescence at 680 nm compared to 600 nm is a secondary indicator of dysplasia.

Diagnostic instruments which detect autofluorescence can be divided into two general groups. The first subdivision includes instruments which utilize fiberoptic probes to perform essentially point measurements on the tissue. The second subdivision includes instruments which produce detailed, two dimensional images. Point detection instruments have the advantage of providing more complete spectral information on the tissue, but are too slow for routine screening of large tissue areas and may miss small regions of dysplasia. Fluorescence imaging endoscopes are more appropriate for screening large tissue areas such as the colon.

Fluorescence imaging systems designed to sense concentrations of fluorescent markers that have been applied to the region of interest are optimized for the measurement of relatively high fluorescence levels, do not describe the additional instrumental features required to measure inherently weak autofluorescence. In particular, they do not describe a method for providing sufficient out-of-band filtering for the excitation illumination that would allow the effective measurement of autofluorescence, which typically is reduced in intensity, compared to the excitation intensity, by a factor of 1000 or more.

Fluorescence imaging endoscopes which are specifically designed to measure autofluorescence can be further divided into groups based on the excitation wavelength chosen and the method for quantifying the degree to which the autofluorescence is reduced. These design choices have a direct bearing on commercial considerations for the instrument since they affect, for example, the number of imaging devices required, the opto-mechanical complexity of the instrument, and the handling characteristics of the instrument in actual use.

Existing fluorescence imaging endoscope systems use visible blue light near 440 nm for the excitation wavelength, resulting in fluorescence peaks around 500 nm. These instruments use Helium-Cadmium lasers at 442 nm as a bright, easily controlled source for the excitation light. The high cost of Helium-Cadmium lasers makes them impractical as sources for commercial instruments.

Multiple cameras and mechanically switched optical components and/or filters require the use of endoscopes based on coherent imaging fiber bundles, so that the cameras and filters can be located at the proximal end of the endoscope where there is room for them. The coherent fiber imaging bundles introduce significant light losses and do not provide as sharp an image as those now available with video endoscopes.

SUMMARY OF THE INVENTION

The present invention relates to imaging endoscopes and in particular to an endoscope system and method for imaging autofluorescence from epithelial tissue to highlight regions of dysplasia. The system for detecting dysplastic tissue uses the autofluorescence of mucosal tissue such as that found in the colon, the esophagus, the oral cavity, the cervix and the lung. The fluorescence imaging apparatus for an endoscope of the present invention utilizes a selected range of excitation light wavelengths and a fluorescence normalization method. These choices provide for an improved endoscope which requires one, non-intensified, imaging detector at the distal tip of a video endoscope for both white light imaging and fluorescence imaging. The imaging detector can be a pixellated integrated circuit device such as a CMOS imaging device, charge coupled device (CCD) or other small two dimensional imaging sensors that can detect in the visible and infrared ranges.

The system of the present invention has the ability to switch back and forth between white light and fluorescence visualization methods electronically, requiring no moving parts within the endoscope itself. The elimination of cameras and imaging optics at the proximal end of the endoscope significantly improves its handling characteristics. A computer-based imaging system allows quantitative images of the tissue to be displayed, at refresh rates of up to 10 Hz or higher, for example. A preferred embodiment uses easily seen, false-color overlays which indicate the likely areas of tissue dysplasia. By "false color" we mean that a color value is assigned to a particular level of fluorescence intensity for each pixel. A data processing system can be programmed to provide a color system suitable for imaging a given type of tissue condition. The system can be used either with color wheel (e.g., using a monochrome CCD) video endoscopes or with color imaging sensor endoscopes.

In a preferred embodiment, near ultraviolet light is chosen as the excitation wavelength, as described in Wang, et al., U.S. Provisional Application No. 60/072,455, Jan. 26, 1998. This choice in the range of 300-420 nm reduces or eliminates the need for additional filters between the tissue and the imaging detector due to the fact that standard, electronic imaging sensors, as used in video endoscopes, are insensitive to the excitation light. Visible red light, to which the imaging detector is very sensitive, is chosen to illuminate the tissue for the purpose of acquiring a reference image. This reference light is passed through the same optical guide as the excitation light, and illuminates the tissue with the same normalized spatial distribution and angular distribution as the excitation light. By correlating the spatial intensity and angular distribution of light used for the reflected image and the light for the fluorescence image, a more accurate and diagnostically useful imaging system is provided. This system of the present invention allows the reference image to be used to normalize the fluorescence image so that local reductions in fluorescence intensity can be accurately quantified. In another preferred embodiment, using color wheel (monochrome CCD) video endoscopes, the reference light and excitation light are applied sequentially. In another preferred embodiment, using color CCD video endoscopes, the fluorescence excitation light and reference light are applied simultaneously.

Figure 1:
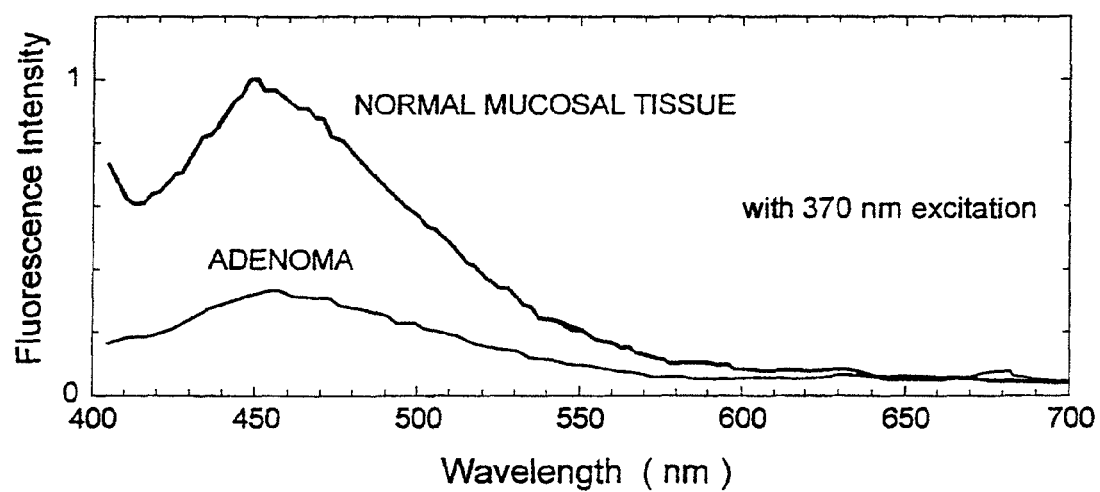
FIG. 1 is an illustration of the fluorescence spectrum of normal and dysplastic colon tissue due to excitation with UV light at 370 nm.

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

DETAILED DESCRIPTION OF THE INVENTION

The present invention relates to systems and methods for imaging autofluorescence from epithelial tissue to highlight regions of dysplasia. The tissue autofluorescence imaging system in accordance with the present invention improves upon the previous state of the art in that, in its simplest form, it can be added on to an existing video endoscope system with no modifications to the endoscope itself, and with only the addition of a shutter in the optical path of the endoscope's visible light source. The handling characteristics of the endoscope are thus not adversely affected by the addition of image intensifiers and external cameras at the proximal end as required by fluorescence imaging systems currently on the market. Switching between normal visible light imaging, in full color, and fluorescence imaging is accomplished by an electronic switch rather than a physical manipulation by the clinician, also required by current systems. The resulting fluorescence video image is processed by a computer so that the diagnostic image seen by the clinician consists of a familiar visible light image (in gray scale) with a false color overlay indicating those areas in the image where the fluorescence from the tissue is reduced in comparison to the fluorescence from normal tissue. This image is much easier to interpret than the combined red/green raw fluorescence images provided by current systems, particularly for red/green color-blind clinicians.

The system of the present invention uses only a single imaging detector at the distal end of the endoscope for acquiring normal color images, fluorescence images and visible reference images. The use of a camera at the distal end is made possible by using fluorescence excitation light at ultraviolet to deep violet wavelengths to which the CCD camera is insensitive or can be made insensitive using a fixed filter. This allows broadband collection of the resulting tissue autofluorescence from blue to red wavelengths, resulting in sufficient light for effective video signals without the need for additional image intensification. Fluorescence imaging in this fashion has been described in-vivo by Wang, et al. as described in U.S. application Ser. No. 09/238,664, entitled "Fluorescence Imaging Endoscope" filed on Jan. 26, 1999, now U.S. Pat. No. 6,537,211, issued Mar. 25, 2003, the entire contents of which is incorporated herein by reference.

Previous autofluorescence imaging systems have depended upon imaging very weak fluorescence at red wavelengths to provide an image to compare with the fluorescence image taken at blue-green wavelengths. Additional image intensification is particularly necessary to provide a usable red fluorescence image. The autofluorescence imaging system and method of the present invention avoids this expense and difficulty by supplying additional visible red light illumination to the tissue for the purpose of obtaining a reference image. To be effective, however, the UV excitation light and the visible reference light must be delivered to the tissue through a common optical guide and exit the same illumination aperture with the same angular distribution. This requires a careful design of the excitation and reference light source optics. The processing of the reference image includes other features, such as histogram analysis, to eliminate artifacts such as visible specular reflections which do not occur in fluorescence images.

The combination of the system features in accordance with the present invention can be realized in several different ways, depending upon the endoscope with which the autofluorescence imaging system is combined. Some of these features can also be built into the endoscope itself in stages as the technology is accepted by clinicians.

In a preferred embodiment, the excitation illumination and reference illumination are generated by the same arc lamp source and delivered to the tissue through the same fiberoptic probe passed through a biopsy channel of the endoscope. In other embodiments the excitation light can be generated with a stand-alone source but delivered to the tissue through UV-transmissive illumination bundles built into the endoscopes as replacements to the standard, UV-absorbing glass bundles. The reference illumination is derived from the normal white light illumination source by switching in a red-pass filter that absorbs light at blue and green wavelengths which can interfere with imaging the predominately blue fluorescence. A deep red light source or near infrared (e.g., at 670 nm or above) can be used without affecting the normal visible illumination and can be combined with a dichroic element for delivery along a common optical path. In further embodiments, the excitation light source can be combined with the standard, white light illumination source and delivered to the tissue through an endoscope with UV-transmissive fiberoptic illumination bundles. A rotating wheel light source can also be modified to produce four colors, ultraviolet, blue, green and red, to perform both the fluorescence imaging and the visual imaging.

Figures 2A, 2B:
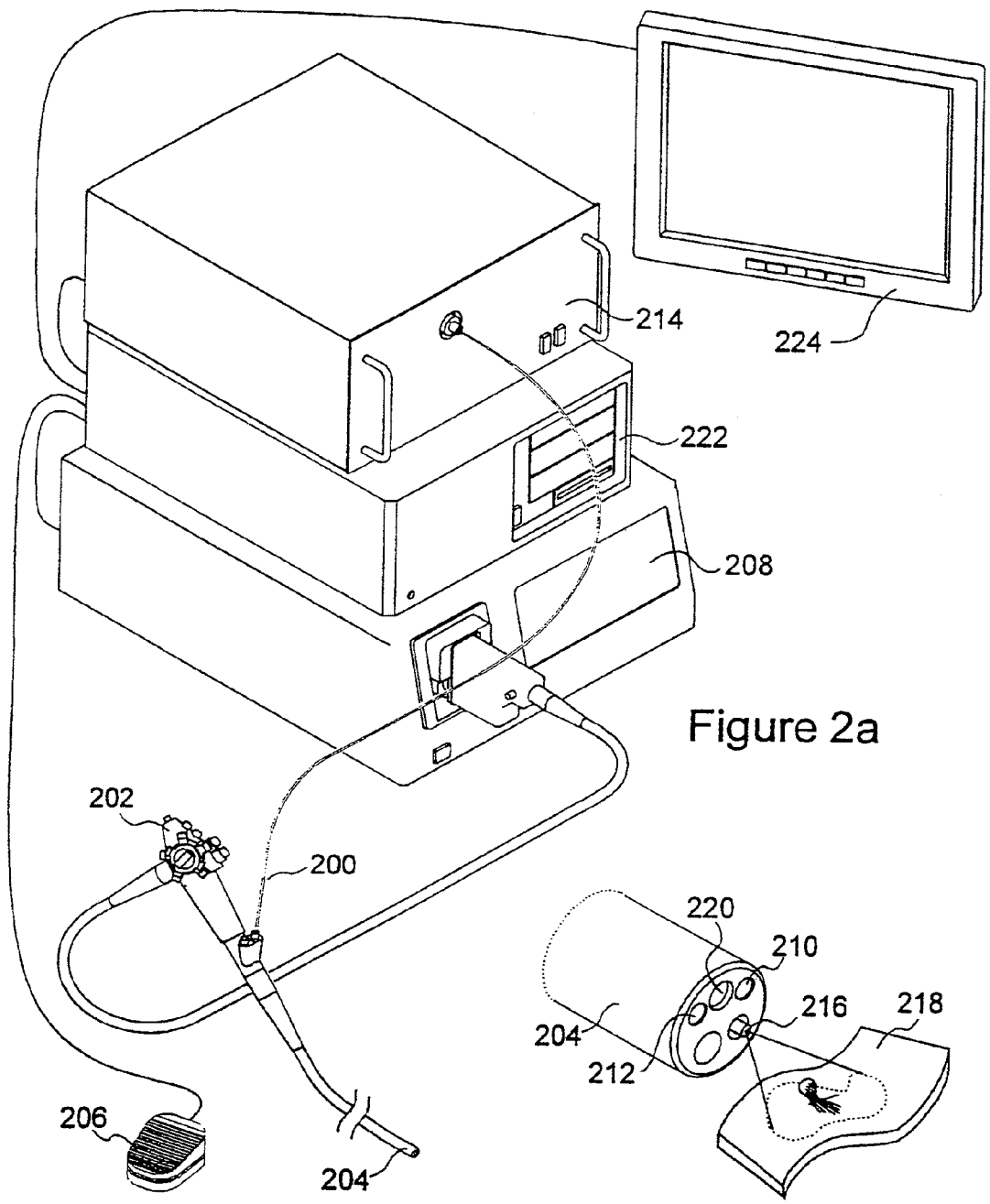
FIGS. 2a and 2b are diagrams of the fiberoptic delivery probe system in accordance with the present invention.

FIGS. 2a and 2b show the general components of a preferred embodiment in which the excitation light and the visible reference light are delivered to the tissue through a separate fiberoptic probe. The fiberoptic probe 200 is passed through a biopsy channel of a standard video endoscope 202 with its tip finally placed at or near the distal tip of the endoscope 204. When a footswitch 206 is depressed by the clinician, the normal white light illumination from the endoscope's light source and video processor 208 is switched off with a shutter. This white light normally illuminates the tissue through the two fiberoptic illumination ports 210 and 212 on the distal tip of the endoscope. Simultaneously, a complementary shutter in the excitation and reference illumination source 214 is switched on so that excitation and reference light can pass through the fiberoptic probe 200. The excitation and reference light exits the tip of the fiberoptic probe 216 and illuminates the tissue 218. The video image detection system 220 transmits the resulting fluorescence image signal and reference image signal back through the endoscope 202 to the video processor 208 where they are converted into different color channels R and B in a standard R,G,B National Television Standards Committee (NTSC) video format. These two channels are digitized with a video framegrabber in the computer system 222. The digitized fluorescence and reference images are processed together in real time to quantify image regions where the fluorescence is reduced compared to normal tissue. Reduced fluorescence is the primary indicator of dysplasia. Areas of the tissue which are likely to be dysplastic are highlighted with false color in a processed image of the tissue which is displayed on a computer monitor 224 and updated at a rate of up to 10 Hz. The preferred embodiment shown in FIGS. 3a and 3b is thus an add-on component to an existing endoscope/video processor system which only requires the addition of an internal shutter to the white light source in the endoscope system's video processor. For color-wheel (monochrome CCD) video endoscopes, the excitation light source 214 is constructed to provide sequential excitation and reference illumination as described in more detail hereinafter. For color-CCD video endoscopes the excitation light source 214 provides simultaneous excitation and reference illumination, also described in more detail hereinafter.

The autofluorescence imaging system demonstrated by Wang, et al. used an argon-ion laser as a UV excitation source. Other laser sources can be used including solid state lasers, such as gallium nitride laser diodes, operating at wavelengths in the range of 380 nm to 420 nm, which have smaller size and low power operation. The systems in accordance with the present invention uses a mercury arc lamp as a source of UV excitation with a spectral band around the 365 nm mercury line. The mercury arc source is smaller, and less expensive than the argon-ion laser, requires relatively little power and is air-cooled. For the autofluorescence imaging systems used with color wheel (monochrome CCD) video endoscopes, the current to the arc lamp can be pulsed. In the color wheel video systems, the normal light source provides red, green and blue light pulses sequentially during a 33 ms video frame which are combined with the video processor to provide a color image. In the autofluorescence imaging mode these systems replace the normal blue light pulse with a UV pulse and the green light pulse with a (nominally red) reference light pulse transmitted through the same optical fiber as the UV pulse. By pulsing the arc lamp current for the 8 ms period that the blue light is normally on, the UV source can provide as much or more excitation fluence to the tissue than it could if the CW lamp intensity was integrated over the full 33 ms video frame period.

With both color wheel video systems and color CCD video systems the autofluorescence imaging mode is initiated with a footswitch which controls complementary shutters on the excitation/reference light source and the normal endoscope white light source. Shutting off the normal endoscope illumination is required in order to image the weak fluorescence from the tissue. Two different autofluorescence imaging modes can be used. In one mode, a single frame of the false color overlay from the processed autofluorescence image is combined with the immediately preceding (or following) color image and frozen on the computer screen. In the second mode the processed fluorescence image is updated continuously (at about 7.5 Hz to 10 Hz allowing for the image processing time) for as long as the footswitch is depressed. In the continuous operation mode the visible image is shown as a gray scale (since it is taken with a monochrome reference illumination) with false color overlays showing regions of likely dysplasia.

Figure 3:
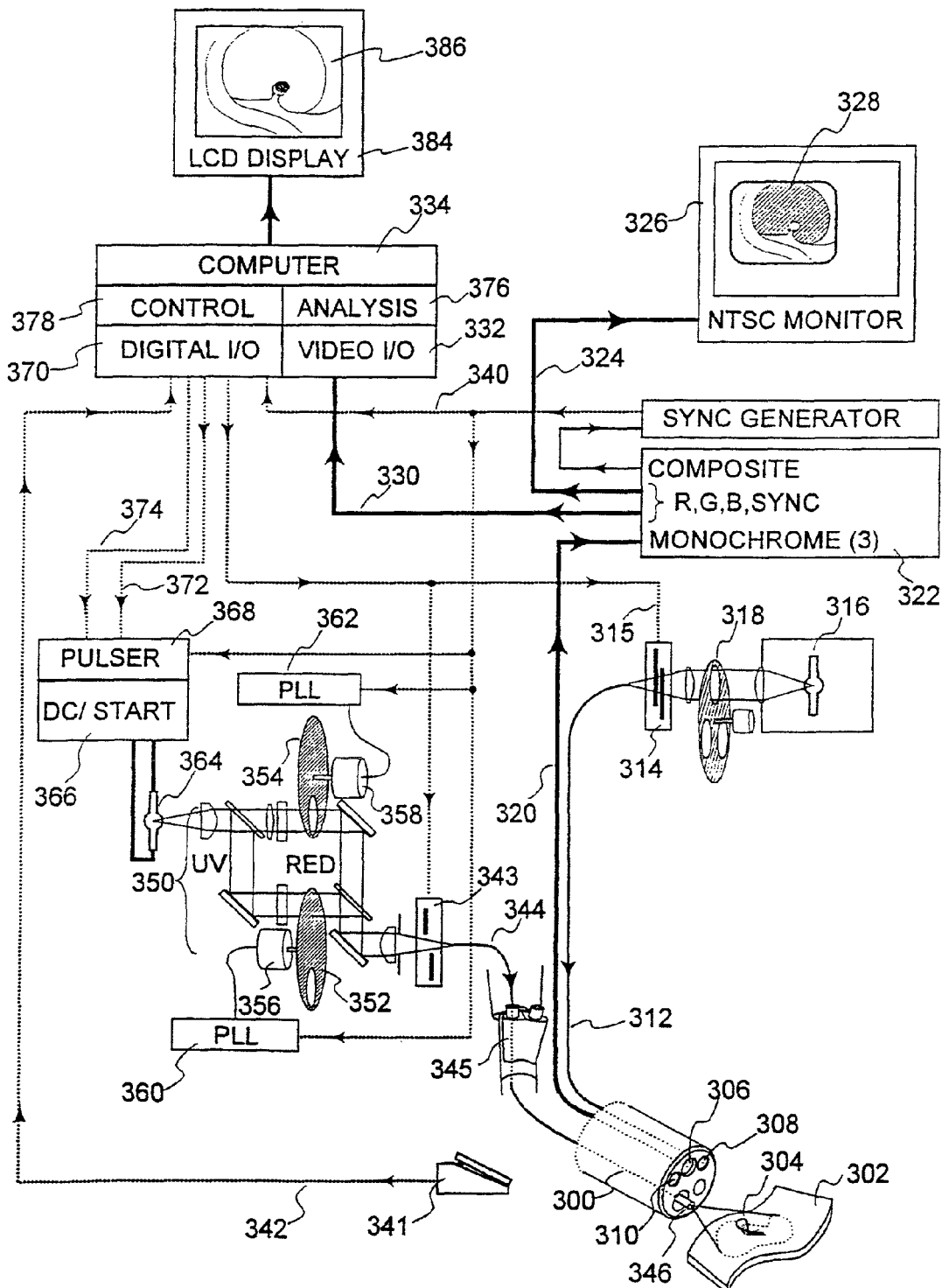
FIG. 3 is a schematic diagram of an embodiment of the fluorescence imaging endoscope of the present invention which uses a separate fiberoptic light guide to deliver the UV excitation light through a biopsy channel of a color-wheel (monochrome CCD) video endoscope.

FIG. 3 shows an overall schematic diagram of a preferred embodiment of the fluorescence imaging system for use with color wheel (monochrome CCD) video endoscopes. For normal mode of operation of the color wheel video endoscope, the distal tip of the endoscope 300 is inserted into the hollow organ of the body to observe an area of tissue 302 which may contain a region which is dysplastic 304. The CCD imaging device and lens subsystem (the video camera) 306 is flanked on either side by the normal illumination apertures 308 and 310.

The normal illumination light is carried by a fiberoptic bundle 312 which extends through the length of the endoscope and bifurcates near its distal tip, terminating at apertures 308 and 310. A shutter 314 between the illumination source and the fiberoptic bundle, controlled by a digital signal 315, allows the white light illumination to be turned off without turning off the source lamp 316. In the type of endoscope shown, the normal color image is obtained by combining three, successive images taken with red green and blue light pulses provided by a rotating filter wheel 318. The CCD detector in this type of endoscope is sensitive to all wavelengths between 400 nm and 700 nm, but is insensitive to UV excitation wavelengths around 365 nm which are used to excite the autofluorescence. This is due both to the design of the silicon sensor array and to the choice of optical materials used to physically protect the surface of the array. The CCD detector continuously integrates all of the light which falls on its surface so the illumination must be shuttered off while the CCD rows are shifted down to the readout electronics or else a streaking effect will be seen on the image. The red, green and blue light pulses have a duration of about 6 ms followed by a dark period of 5 ms during which the camera pixels are read out, yielding a total video frame period of about 33 ms or 29.97 frames per second to meet the NTSC standard. The analog readout signal form the CCD camera is carried through a cable 320 to the endoscope video processor 322.

The three successive monochrome images are digitized and combined into a standard color video signal at the end of the video frame. The processor has two groups of standard red, green, blue (RGB) plus synchronization outputs. One output group of color signals 324 goes to the endoscope's video monitor 326 to display the normal color image of the tissue 328. Another group of color signals 330 goes to a video framegrabber 332 in the fluorescence imaging computer system 334 which will acquire and process the autofluorescence and reference images. A standard composite color signal output 336 from the video processor goes to a synchronization circuit 338, based on a National LM1881 Video Sync Separator. This synchronization circuit 338 determines when the interlaced even and odd fields occur in the video signal and outputs a binary digital signal 340 which is high during the odd field and low during the even field. This signal 340 is used throughout the fluorescence imaging system to synchronize its functions to the timing set by the endoscope's video processor.

To engage the autofluorescence imaging mode of operation, the clinician depresses footswitch 341 which sends a signal on cable 342 to the computer 334. At the appropriate time, synchronized to the next opportunity as determined by the synchronization signal 340, a signal is sent out on the shutter trigger line 315 to shutter 314 on the normal illumination source and the shutter 343 on the excitation/reference light source. These shutters are complementary, so that the signal on line 315 opens shutter 343 and simultaneously shuts shutter 314. The excitation and reference light pulses, generated by the rotating shutter wheels in the optical group 350, then pass into the fiberoptic probe 344. Probe 344 is inserted into a biopsy channel opening 345 and slid down the channel until its end window 346 is either at or just beyond the distal tip of the endoscope 300. The excitation and reference light pulses illuminate the central portion of the endoscope's visual field. The angular extent of the illumination depends on optical elements 350, the fiber numerical aperture, and the optical characteristics of the fiberoptic probe end window 346.

The excitation and reference light pulses must occur during two of the three normal illumination pulse periods for the autofluorescence and reference images to be properly acquired. These images appear on the next video output frame on two of the three video output channels from the endoscope video processor. The appropriate timing is accomplished by rotating shutters 352 and 354 in the excitation (UV) and reference (RED) light paths, respectively, of the optical group 350. The shutters are driven by direct current (DC) motors 356 and 358 which rotate at a speed which can be controlled by varying their supply voltage. A fiducial hole near the rim of the shutters, combined with an optical source and detector, generates a reference pulse for each which marks its phase as it rotates. A phase-locked loop (PLL) 362 and 360 for each motor, 358 and 356, respectively, adjusts the motor's voltage so that the reference pulse for each matches the rising edge of the synchronization pulse 340 marking the beginning of the odd video field.

By positioning the hole in the shutters appropriately the excitation light pulse and the reference light pulse can be timed to the exposure periods of the camera. The excitation pulse is timed to match the normal blue exposure since this exposure period is somewhat longer (8.1 ms) than the others. The reference light pulse is timed to match the normal green light exposure (5 ms) since it is the next longest of the normal exposure periods. The normal red exposure period, which immediately follows the normal blue exposure period, is not currently used, but can be employed to obtain additional autofluorescence or reference images or an additional visible reflectance image for other spectroscopic analyses. During the excitation exposure the current to the mercury lamp can be boosted to a higher level to increase the excitation light output. The lamp power supply utilizes a DC current section 366 to maintain the idle current and start the lamp.

A computer-controlled, pulsed current section 368, connected in parallel with the DC section 366, can rapidly switch in multiple, parallel-coupled, constant-current sources to vary the output power of the lamp as required by the imaging system. The current pulses are synchronized to the video system using the same synchronization pulse 340 that serves to lock the rotating shutters. The computer digital input/output (I/O) section 370 outputs a digital pulse 372 which is combined with the timing pulse 340 to boost the lamp current during the excitation exposure. The number of constant current sections which are triggered in parallel can be varied by a set of digital control lines 374 as required. If the tissue is sufficiently close to the excitation/reference delivery probe window 346 then no boost may be required. If the peak value of the autofluorescence image drops to a minimum acceptable level, as determined by the computer image analysis program 376 as monitored by the overall control program 378, then additional current boost sections are enabled as required for the next exposure.

Once the autofluorescence image and the reference image have been acquired by the digital framegrabber in the computer then the analysis can begin. A reflectance (non-fluorescing) image taken with an endoscope camera system measures the brightness of the tissue surface in its field of view. To the extent that the tissue surface is a Lambertian (non-specular) reflector, the reflectance image signal (as digitized by the video framegrabber for each discrete pixel in the video image) is proportional to distance of the tissue from a single illumination source (or a weighted distance from multiple sources), and to the integrated energy of the excitation illumination during that video frame. The end window 346 of the excitation/reference delivery probe is not in the direct line-of-sight from the camera lens to the tissue so there will be visible shadows. A reflectance image can thus be used to measure the excitation illumination at the tissue surface visible to the camera, including the presence of shadows in the autofluorescence image. Note that this is only true if the excitation illumination and the visible illumination emanate from the same aperture with the same transverse intensity profile and angular divergence as provided by the design of the source as described hereinabove. A visible reflectance image taken with light from the illumination bundles of a standard endoscope, for instance, is not acceptable for determining the excitation illumination from a separate optical fiber passed through a biopsy channel of that endoscope. Note also, however, that the same aperture/same divergence condition can be satisfied by passing both the excitation and the reference light pulses through the illumination bundle of the endoscope.

The sequence of steps for obtaining a false color indication of dysplasia probability using the visible reference image along with the autofluorescence image proceeds as follows. The two images are first corrected for the gamma factor applied to the video signal by the video processor which is generally connected to a video monitor rather than a framegrabber. This insures that the digitized images acquired by the framegrabber in the computer are linear functions of the illumination fluence (time-integrated intensity). The two images are then normalized to their peaks, which is generally a region of non-dysplastic tissue somewhere in the visual field. There are a few pixels in the reference image which are saturated due to specular reflections of the reference illumination. These are effectively eliminated by producing a histogram of the reference image and normalizing the image to a peak value. This generally includes about 99% of the pixels.

All normalized reference image pixels above a value of 1 (the specular reflections) are then reset to a value of 1. There are no specular reflections in the autofluorescence image so such a histogram-based normalization is not necessary. On a pixel-by-pixel basis the autofluorescence image value is then divided by the corrected reference image value to produce a ratio image. This division is performed only when the autofluorescence and reference image pixel values are above a minimum threshold condition to insure that the analysis is not attempted with too little illumination to provide a reliable measurement.

If a ratio image pixel value falls below a predetermined value (typically one-half to one-third) then that pixel represents a region of reduced fluorescence on the tissue surface which is indicative of dysplasia. The corresponding pixel in the processed output image can then be set to a false color state to indicate the relative probability of dysplasia. If the ratio image pixel value is below ⅓ the red value of the corresponding processed output image pixel it is set to the value of the reference image and the green and blue values of that pixel are set to zero (it is a shaded red, indicating a high probability of dysplasia). If the ratio image pixel value is ½ to ⅓, then the green value of the processed output image pixel it is set to the reference image value and the red and blue values are set to zero (it is a shaded green, indicating a moderate probability of dysplasia). If the ratio image pixel value is above ½ then the red, green and blue values of the processed output image pixel are all set to the reference image value (it is a shaded gray, indicating the probability that the tissue is normal). This processed output image 386 is displayed on an LCD monitor 384 attached to the system computer 334.

Figure 4:
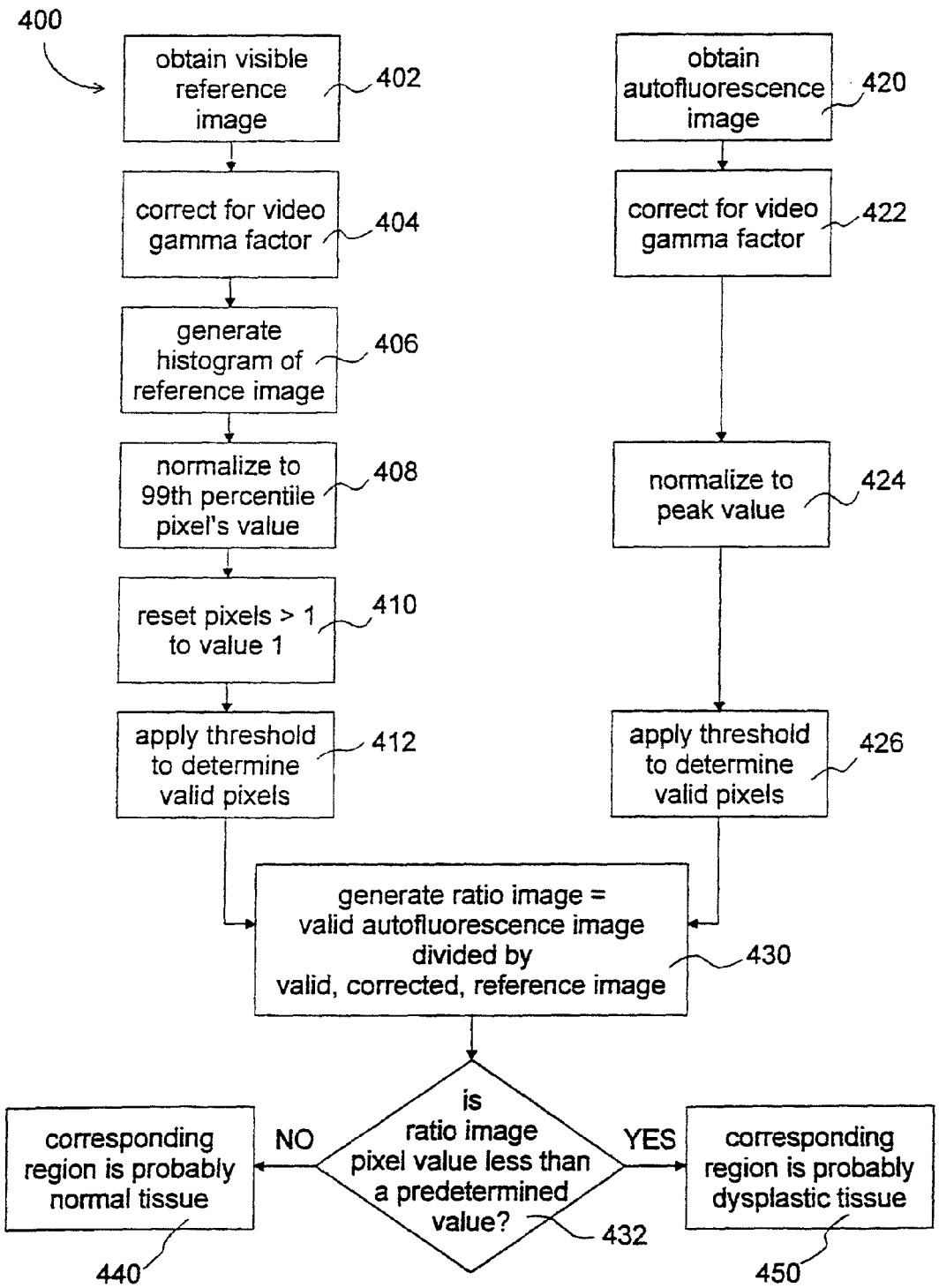
FIG. 4 is a flow chart for the production of the output image.

FIG. 4 illustrates a process sequence 400 after a patient has been prepared the endoscope inserted into the body cavity or human and the distal end thereof has been positioned for imaging of a region of interest. In this particular example, a visible reference image is obtained 402. This reference data is corrected 404, a histogram is generated 406, the data is normalized 408, selected pixels are reset 410 and a threshold value is applied 412. After a fluorescence image is obtained 420, the image is corrected 422, normalized 424, a threshold applied 426, and a ratio image is generated 430. The resulting output image or representation is then compared 432 to a reference, and a given region is determined to be normal 440 or dysplastic 450.

Figure 5:
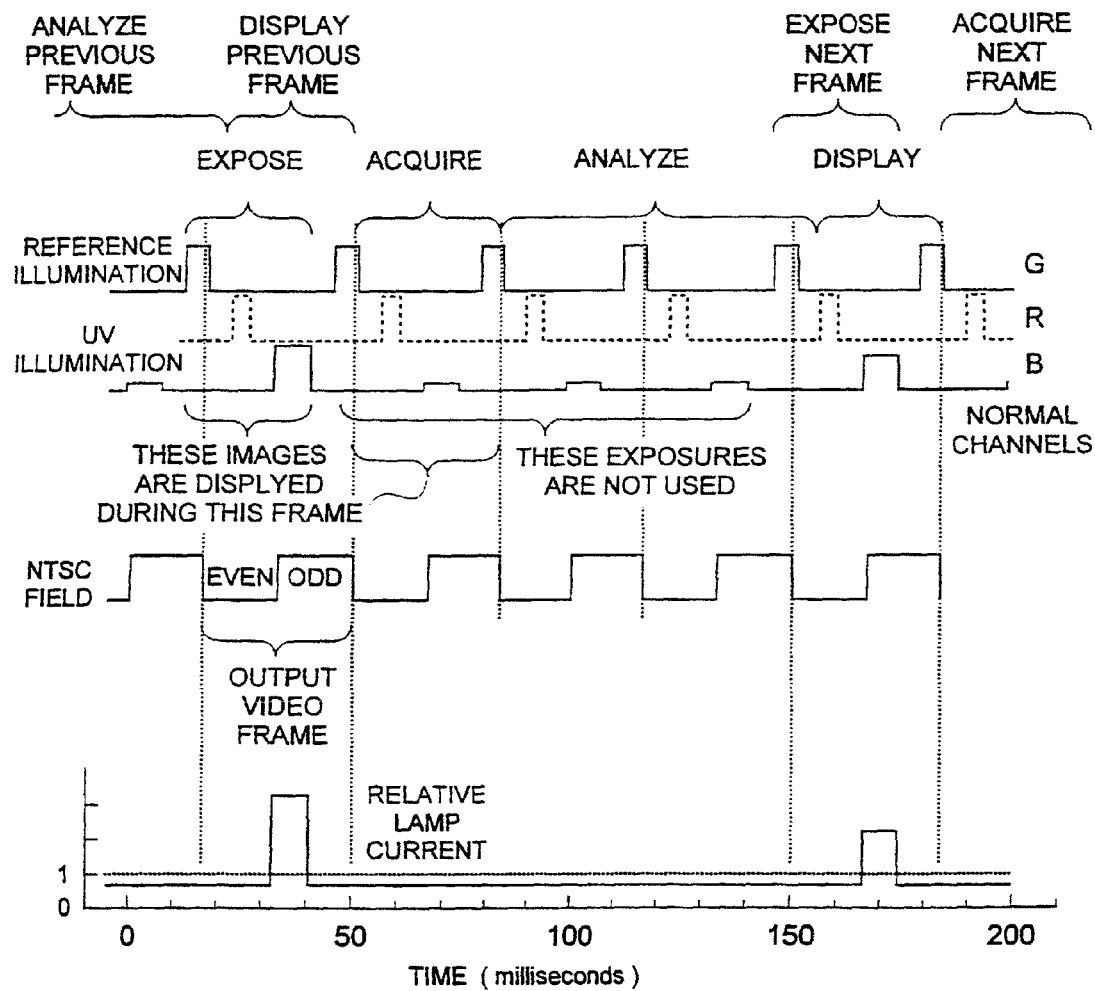
FIG. 5 illustrates a timing diagram for the image acquisition, analysis and display process in accordance with the present invention.

FIG. 5 shows a timing diagram for one cycle of the imaging process. The maximum video output rate is 29.97 Hz as set by the NTSC standard. The diagram indicates a system which requires one frame time for acquisition, between two and three frame times for analysis, and a fraction of a frame time for transferring the result to the output image buffer. The resulting update rate for the analysis image is 7.5 frames per second. With a single, fast processor, the analysis time can be reduced and the update rate correspondingly increased to 10 or 15 frames per second. The image analysis can also be performed at output rates up to 30 frames per second by, for example, using two processors operating in parallel with only a few frames of delay between acquisition and display. Increased update rates, however, require a reduced upper limit on the pulsed current to the lamp in order to maintain an average lamp dissipation of no more than 100 W. FIG. 5 also shows how the mercury lamp current is boosted only during the blue exposure periods which result in autofluorescence images. At other times the lamp idles at a reduced power.

Figure 6A:
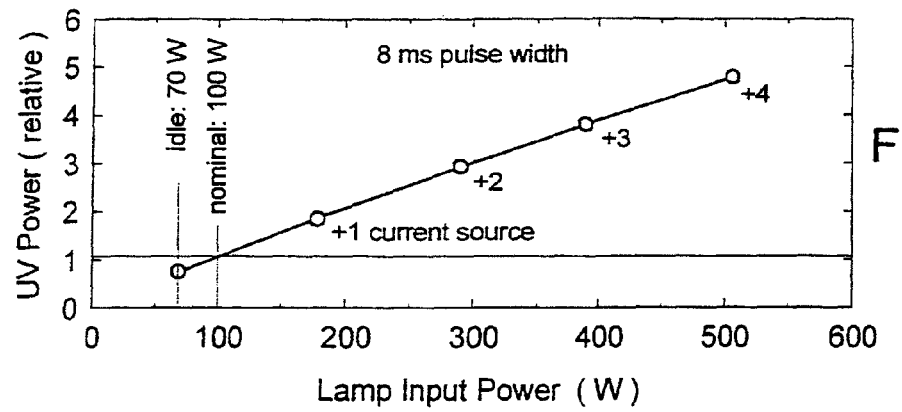
FIGS. 6a-6c illustrates the UV output from a mercury arc lamp as a function of pulsed current in accordance with the present invention.
Figure 6B:
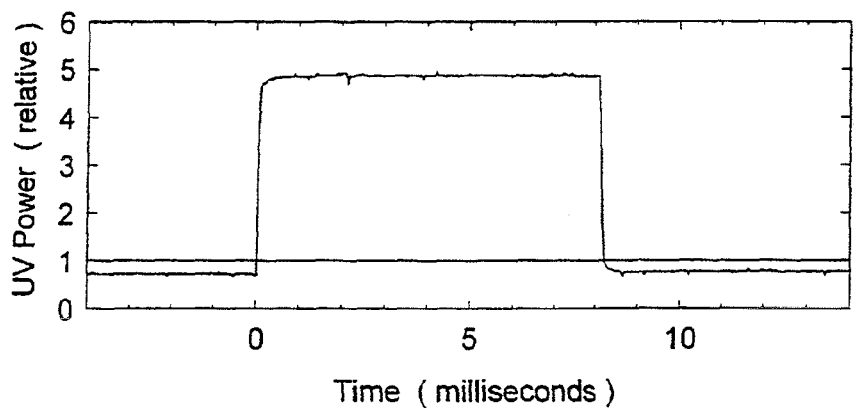
Figure 6C:
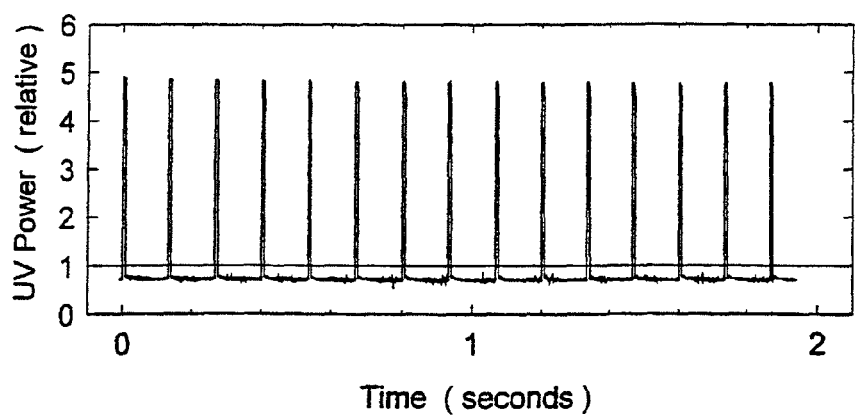

FIGS. 6a and 6b show that the UV output power from a 100 W Hg arc lamp, pulsed for 8 ms above a 70% idle current, is essentially a linear function of its input power to at least a factor of 5 over its nominal rated power. Boosting the lamp current during the UV exposure period increases the lamp output power which, in turn, allows a larger area of tissue to be scanned for dysplasia. It also provides a means for adjusting the output of the lamp for an optimum video exposure on a pulse-to-pulse basis. Since the lamp discharge maintains a nearly constant voltage drop across the arc regardless of current, the lamp output power is essentially proportional to current. About 70% power to the lamp must always be maintained, however, to keep the mercury in the vapor phase. FIG. 6c shows that pulsing the current to a factor of 5 over the rated CW current can be repeated continuously at a rate of 7.5 Hz.

Figure 7:
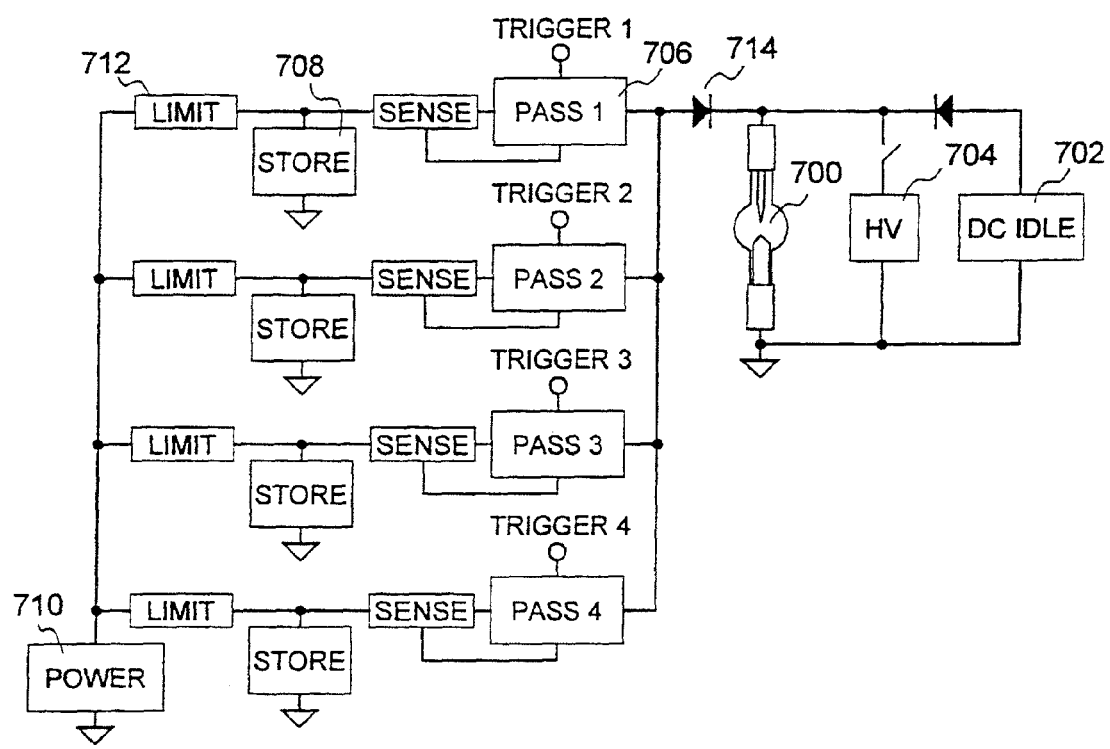
FIG. 7 is a schematic diagram of a computer-controlled, pulsed lamp power supply in accordance with the present invention.

FIG. 7 shows a block diagram of the lamp power supply as it connects to the mercury arc lamp 700. The DC idle current circuit 702 and high voltage (HV) starting pulse circuit 704 are handled by a single commercial power supply designed for CW 100 W mercury arc lamps. The constant current, triggered pulse circuit 706 is designed to match the specific requirements of the fluorescence imaging endoscope. Four of these circuits are connected in parallel so that the output of the arc lamp can be set digitally to one of 5 different power levels (including idle). Each circuit is composed of a power MOSFET switch which adjusts its resistance to keep the passed current at a fixed level, typically equivalent to the normal DC current of 4 amps. These circuits can be individually triggered by a computer whenever their current boost is required to properly illuminate the tissue. Each circuit draws its current from a storage capacitor 708 charged by a power supply 710 through a current limiter 712. This limited current design minimizes the possibility of fault conditions which could overload the power handling capacity of the arc lamp.

Figures 8A, 8B, 8C, 8D:
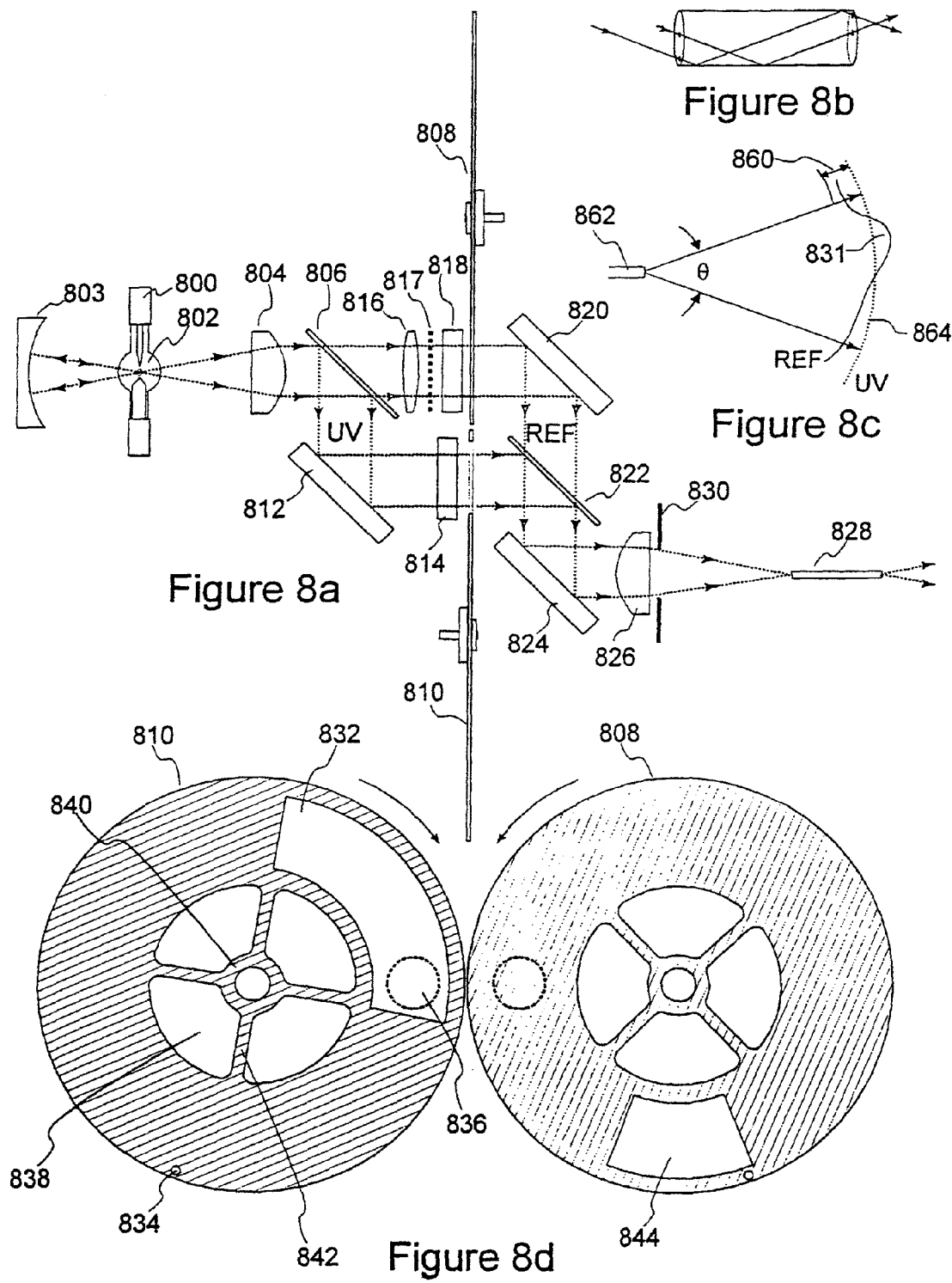
FIGS. 8a-8d illustrate the details of opto-mechanical elements of the pulsed light source in accordance with the present invention.

FIGS. 8a, 8b, 8c and 8d show details of the excitation/reference illumination source optics. A single mercury arc lamp 800 in FIG. 8a is used as the source of both wavelengths because both the UV/violet excitation light and the red/near infrared reference light need to have the same apparent source volume 802 at the distal tip of the endoscope. Small 100 W, mercury arc lamps have arc dimensions of 0.5 to 1.0 mm which are small enough to couple efficiently into the optical fibers used to deliver the light to the tip of the endoscope. Separate lamps can be used for the excitation and reference beams, but the tolerances for the source optics and the alignment of the source arcs are then more critical. In the preferred, single lamp, source design shown in FIG. 8a the light collection optic 804 is shown schematically as a single, fused silica, UV-transmitting lens. In practice either a multiple element lens design or a mirror-based Schwarzschild objective is used to reduce optical aberrations on the collected beam. Such collection optics could also collimate light from the focal volume of a commercial mercury arc lamp with a fixed, pre-aligned, elliptical reflector as an alternative source. The collection optics 804 collimate the light from the lamp so that it can be effectively filtered into UV and visible components by means of a dichroic mirror 806 which reflects UV and/or deep violet wavelengths and transmits visible wavelengths.

Separation into two paths is required so that two rotating shutters, 808 and 810, can produce UV excitation and visible reference pulses at different times during the video frame as described above. A UV-reflective surface coating on mirror 812 immediately after the dichroic mirror reflects nearly 100% of the desired UV light in that path and dumps much of the undesired visible light reflected from the dichroic into its substrate. Additional UV filters represented by element 814 may include absorptive filters such as Schott UG-1 glass as well as multilayer dielectric bandpass filters centered on the 365 nm line of mercury. The UV path rejects visible light to a high degree since the efficiency of the 460 nm tissue fluorescence is only about 0.1%. Leakage of visible source light during the UV exposure period reduces the contrast of the autofluorescence image. Some correction for such leakage is possible during the digital image processing but corrections always add a small amount of noise to the result.

The first element in the reference path is a weak lens 816 to correct for the lower refractive index of the fused silica collimating lens 804 at visible wavelengths as compared to the UV. Note that lens 816 would not be necessary if a Schwarzschild objective is used at the position of lens 804 since such a design uses only mirrors and is thus totally achromatic. An attenuator can optionally be moved into the reference path at position 817 to prevent saturation of the reference image at close inspection distances. This attenuator must be uniform across the area that the reference beam passes through in order to maintain the uniform angular intensity distribution required of the reference illumination. This attenuation can be accomplished with variable, crossed polarizers, differentially-sliding, linear attenuation wedges or electromechanically-switched, fixed-value attenuators. The visible filter 818 in the reference beam path is less critical than the UV filter when sequential excitation/reference beams are used such as in the system shown. The reference beam wavelength is chosen to avoid hemoglobin absorption bands since a significant absorption introduces an error into the analysis which assumes that the reference image is equivalent to a measurement of the excitation illumination intensity. The rotating shutters 808 and 810 follow the filters. Continuing down the visible path after shutter 808 is turning mirror 820 with a broadband visible reflective coating. A second dichroic mirror 822, identical to dichroic mirror 806, recombines the UV excitation beam and the visible reference beam onto a common path. One additional tuning mirror 824 which reflects both UV and visible light directs the two beams towards the focusing optics 826 which couples them into the delivery fiber 828. The turning mirror 824 makes the number of reflections in both the UV and visible paths of the system equal. With equal numbers of reflections, any change in the position of the mercury arc 802 relative to the position of the collection optics 804 results in the same angular deviation for both the excitation and reference beams. Equal deviation angles preserves the overlap of the excitation and reference beams on the tissue. The system as shown in FIGS. 8a-8c, in which the combined beams exit the optical train in the same direction as the incoming beam, also makes the direction of the output beams invariant under translations and small rotations of the optical train as a whole.

The aperture stop 830 in FIG. 8a insures that the UV excitation and visible reference beams have the same angular convergence on entering the delivery fiber 828. The transverse dimensions of the two beams at the position of the focusing optic 826 will invariably be slightly different due to small errors in the positioning of the optics in the two paths and slight differences in the effective emitting volume of the arc at the two wavelengths. The aperture stop 830 is set so that both beams are slightly clipped at their outside edge, insuring that the maximum angular input to the optical fiber is the same for both. FIG. 8b shows that, to a great degree, the input angle to an optical fiber, relative to the fiber axis, is preserved upon each reflection within the fiber. Illumination of a fiber with a collimated beam from a single direction generally results in a cone of emitted light from the opposite end of the fiber which has the same angle relative to the axis. The light is spatially averaged over the exit aperture of the fiber but the angles only slowly spread due to bends in the fiber as it passes down the length of the endoscope. The embodiment shown insures that the normalized angular intensity distribution of the excitation illumination and the reference illumination are closely matched as required by the autofluorescence normalization method. If, for example, the normalized reference illumination locally exceeds the normalized excitation illumination in a region 831 as shown in FIG. 8c, then the analysis falsely indicates reduced autofluorescence in this region. If the normalized reference illumination is greater by a factor of two over the normalized excitation then the analysis provides a false positive indication of dysplasia, where the threshold condition is set to 50%. Similarly, if the normalized reference illumination is a factor of two below the normalized excitation illumination in some region, then the analysis indicates normal tissue even if the autofluorescence was actually reduced by the same factor of two in that region. Such large errors are unlikely in the center of the illumination field but can occur at the edges of the field where the illumination drops to the noise level. The threshold conditions placed on both the reference and autofluorescence images insure that the analysis is not attempted where it is too easily influenced by noise or edge effects. In general, it is described to maintain any variation in the intensity distribution of the reference light as seen at 860 (normalized) at less than 20% relative to the intensity distribution of the excitation light at any point along the optical path between the combiner and the tissue surface. It is most important to achieve minimal variation in intensity at the tissue surface. Thus light exiting the fiber 862 is within the cone defined by the angle θ and variations in intensity at along the wavefront 864 should be less than 20% to minimize the risk of false image.

FIG. 8*d* shows a more detailed view of the rotating shutter design in the excitation/reference source. Each blade rotates once in 33.3 ms, the period of one video frame. The angle subtended by the aperture 832 on the excitation shutter blade 810 corresponds to the 8.1 ms period for the normal blue exposure. The timing of the UV exposure relative to the video frame is set by the phase-locked loop matching the rising edge of the optical pulse through the excitation blade fiducial 834 to the rising edge of the odd field mark on the synchronization signal 340 as shown in FIG. 3. The apparent position of the excitation beam in the optical train is marked by the dotted circle 836. For the relative dimensions of the beam diameter to shutter diameter shown the total rise time of the light pulse is 1.7 ms which is acceptable compared to the total length of the pulse. The blade 810 is thin, light in weight and opaque, made from a material such as stainless steel or glass-fiber reinforced expoxy.

Mining the moment of inertia simplifies locking the shutter's rotation rate with the PLL. Being opaque is important to prevent light leakage. The cutouts 838 around the central hub 840 of the wheels leave thin blade flexures 842 which allow the wheel to flex slightly as it rotates to stay perpendicular to the rotation axis of the motor, minimizing vibration and stress on the motor bearings. The continuous outer edge of the shutter serves to carry the timing fiducial at the maximum distance from the axis where it is most sensitive and serves a safety function as well in the case of an inadvertent touch during assembly and testing. The aperture in the visible reference shutter 844 is positioned to match the normal green or red period of the video timing sequence. This instrument can either provide a single false color image for each footswitch signal or a series of processed images at a submultiple of the 30 Hz video frame rate.

A standard personal computer system can process the acquired data and update the false color image at 10 frames per second which is fast enough to preserve the impression of smooth motion and slow enough to allow a significant increase in the pulsed lamp current. Operation at lower submultiples of 30 Hz (7.5 or 6 Hz) still provides adequate real-time feedback and permits higher pulsed currents (and thus brighter WV illumination) without exceeding the nominal 100W average power dissipation in the lamp.

Figure 9A:
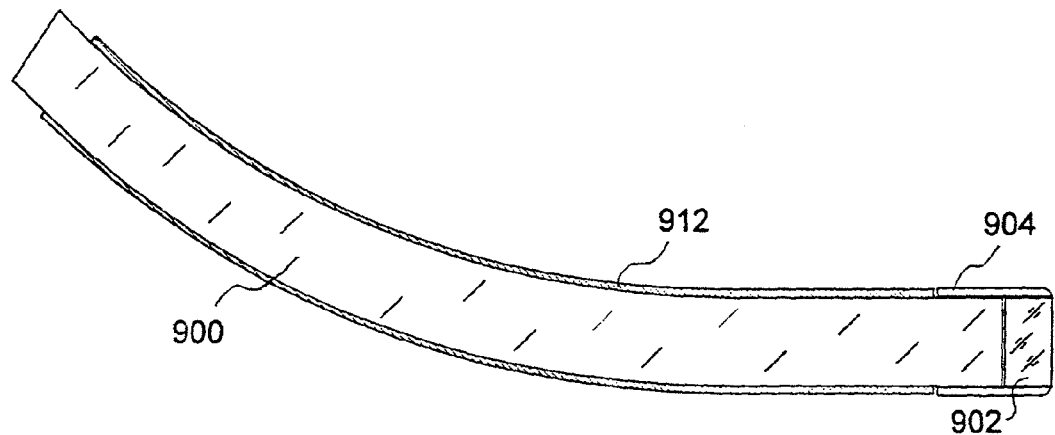
FIGS. 9a-9c illustrate the construction of the optical delivery fiber used in accordance with the present invention.
Figure 9B:
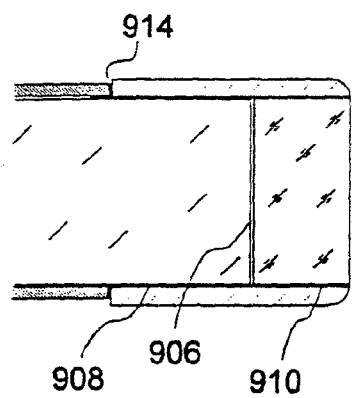
Figure 9C:
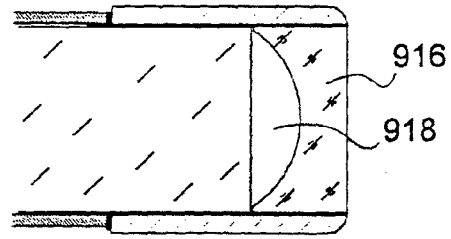

FIGS. 9*a*-9*c* show details of the optical fiber probe which delivers the UV and reference light pulses from the source described above, through a biopsy channel in the endoscope, to the tissue at the distal tip of the endoscope. The delivery fiber 900 must transmit both the UV and the reference light wavelengths, couple efficiently to the light source and be sufficiently flexible so that it doesn't significantly affect the flexibility of the endoscope tip.

The fibers can be made with multiple, small-diameter fused silica fibers, but the preferred system uses a single, UV-transmitting acrylic fiber with a diameter of from 1.5 to 2 mm. One particular acrylic fiber that is suitable is the Raytela Polymer Optical Fiber made by Toray Industries, Inc. The single fiber system increases coupling efficiency by eliminating the packing fraction losses of multifiber bundles. Eliminating the multiplicity of internal cavities also increases the reliability of the disinfection process between procedures.

A window 902 at the tip of the probe is held on with a sleeve 904 and low-fluorescence epoxy in the gaps 906, 908 and 910 as shown in FIG. 9*b*. A thin, bio-compatible, sheath of heat-shrink tubing protects the thin cladding of the optical fiber. A band of epoxy at position 914 in the gaps between the fiber 900, the sheath 912 and the sleeve 904 seals the probe for disinfection and holds the sheath in place. This type of fiber has a numerical aperture, NA, of 0.5 which means that the light is emitted over a 60 degree, full-angle cone. Probes with a plane window illuminate only about half of the 120 degree maximum field of view for a typical endoscope.

FIG. 9*c* shows a negative lens 916 used in place of the plane window 902 with an air gap 918 between the lens and the end of the optical fiber. The negative lens increases the illuminated field of view at the expense of excitation illumination intensity. Additional negative lenses would increase the field further. Probe designs such as that of FIG. 9*c* are optimized for scanning large areas while the plane window design of FIG. 9*b* is optimized for scanning more localized regions of dysplasia. These windows or lenses can be made of fused silica or UBK-7 to optimize UV transmission. Millimeter thicknesses of common glasses such as BK7, however, do not absorb a significant fraction of the excitation illumination. The lenses or windows can also be made from a UV-transmitting, blue-blocking, red-transmitting glass such as Schott UG-1 if the level of blue fluorescence in a particular type of delivery fiber degrades the fluorescence image. Such additional filtration has not been required in probe designs using the Raytela fiber.

In a preferred embodiment, constructing the above probe from a UV-transmissive plastic will reduce the cost, compared to a fused silica construction, to the point where the entire probe can be disposed after a single use.

Figures 10A, 10B:
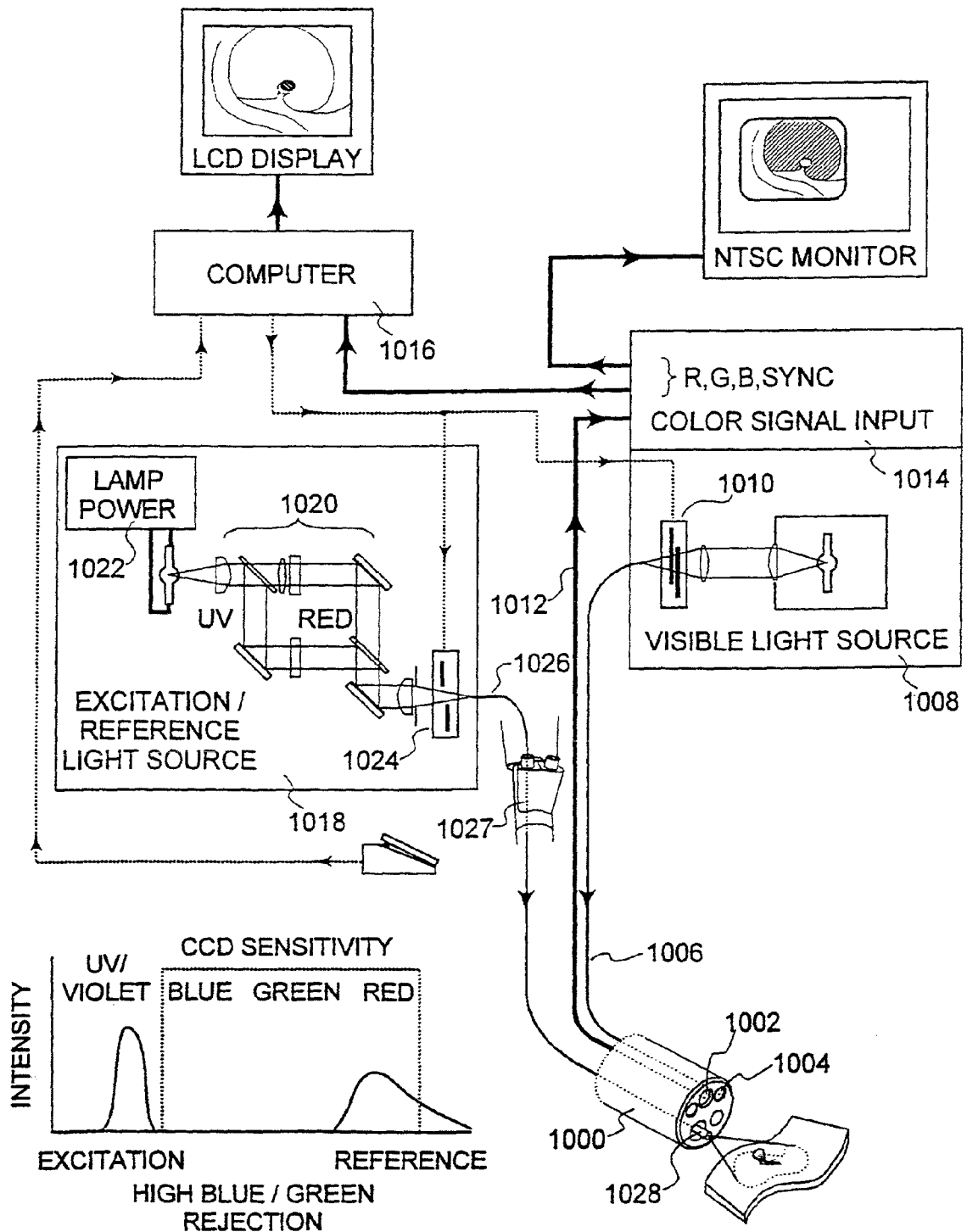
FIGS. 10a-10b are schematic diagrams of a preferred embodiment of the imaging system which uses a separate fiberoptic light guide to deliver the UV excitation light through a biopsy channel of a color CCD video endoscope.

FIGS. 10*a* and 10*b* show how the autofluorescence imaging system shown in FIG. 3 can be modified for use with a standard, color-CCD video endoscope 1000. In this type of endoscope the image detection system 1002 detects red, green and blue light simultaneously with discretely filtered pixels on the CCD detector. The illumination source 1008 for this type of video system emits continuous, broadband, white light which still needs to be turned on and off with a shutter 1010 for use with the modified autofluorescence imaging system. In this embodiment the excitation/reference light source 1018 produces the two wavelengths simultaneously with the optical train 1020, with a high rejection of light at blue and green wavelengths (greater than 1000:1) where the autofluorescence peaks. The spectrum of the continuous illumination is shown in FIG. 10*b*.

For autofluorescence detection the complementary shutters 1010 and 1024 are triggered as before, causing the tissue to be illuminated with both the excitation light and reference light simultaneously. The UV-induced autofluorescence (primarily at 460 nm) is then detected by the blue-responsive pixels in the CCD camera. The red reference reflectance image is simultaneously detected by the red-responsive pixels. Color CCD cameras typically use electronic shuttering so that they don't need a dark period for their readout. In this embodiment, the rotating shutters in the excitation/reference light source 1018 are either stopped in an open position with a detent, or eliminated altogether if the autofluorescence system is to be used only with color video endoscopes. The UV illumination thus lasts for the full 33 ms of the frame, increasing the integrated visible fluorescence and reference signals and eliminating the need for a pulsed current supply. The lamp current supply 1022 could still be pulsed occasionally for single images without overheating the lamp. The analysis would proceed as before with the reference image appearing on the red channel of the RGB NTSC signal and the autofluorescence image appearing on the blue channel.

In the fluorescence image endoscope in accordance with the present invention, both the UV-excitation light pulse and the visible-reference light pulse are delivered to the tissue through an optical probe inserted through a biopsy channel of a standard endoscope. The excitation and reference light could alternatively be passed through the illumination bundle of an endoscope if that bundle were to be modified to transmit UV as well as visible wavelengths. The requirement would remain that the excitation light and the reference light, even if generated by different sources, have the same angular distribution as they exit the distal tip of the endoscope.

FIGS. 11a-11d show an embodiment of the autofluorescence imaging system which uses a UV-transmissive endoscope, a standard white light source for normal imaging, a separate excitation light source and a coupling box. This system is used if a modified endoscope were to be developed before a dedicated light source combining the white light, excitation and reference functions in one unit. In this intermediate instrument, the adapter box 1100 would fit between the standard white light illuminator 1102 and the electrical/optical connection plug 1104 of the UV-transmissive video endoscope. The optical connection plug 1106 normally fits directly into the visible light source 1102 to collect the illumination light and pass it into the illumination bundle of the endoscope. In this embodiment the optical connection plug 1106 would fit instead into the adapter 1100 and an identical optical connection plug 1108 on the opposite end of the adapter would fit into the visible light source 1102. A set of imaging optics 1110 would transfer the light emitted from the exit aperture of plug 1108 to the entrance aperture of plug 1106. This set of imaging optics would also transfer excitation light from a separate light source, exiting the optical fiber 1112 to the entrance aperture of plug 1106.

Figure 11C:
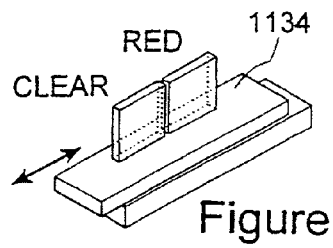
FIGS. 11a-11d are schematic diagrams of a preferred embodiment of the imaging system which integrates the UV-transmissive illumination guide into the endoscope and connects an external UV excitation source to a standard white light source with an adapter module.
Figure 11B:
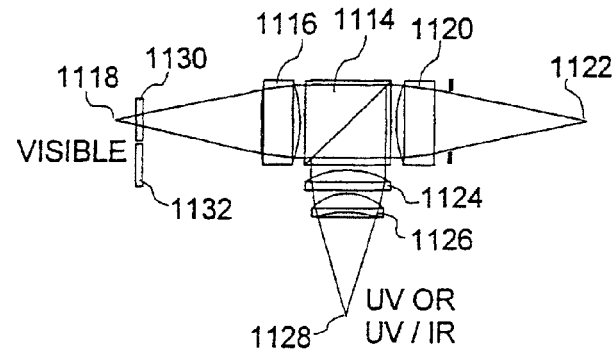
Figure 11A:
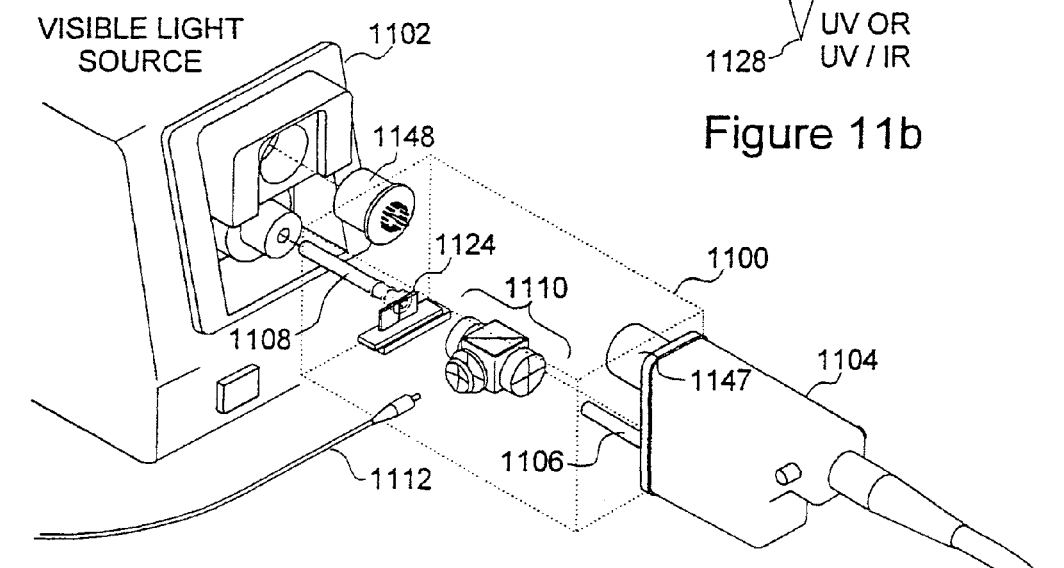
Figure 11D:
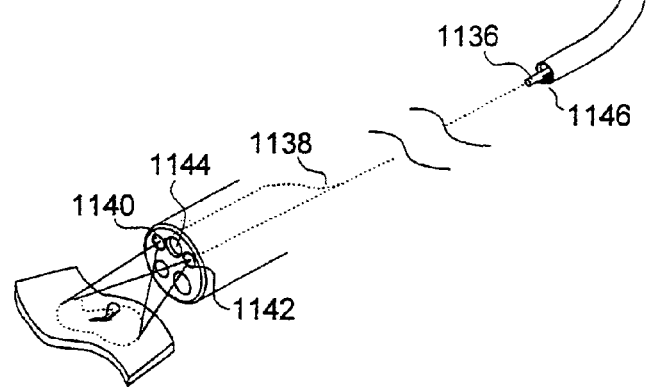

The imaging optics set is detailed in FIG. 11b. The combination of the excitation illumination onto a common axis with the visible illumination is accomplished with a dichroic beamsplitter cube 1114. An achromat 1118 collimates visible light expanding from a point 1118 on the exit aperture of plug 1108. A second achromat 1120 refocuses this light onto point 1122 on the entrance aperture of plug 1106. A set of fused silica lenses 1124 and 1126 nominally collimate the light from point 1128 on the exit aperture of the excitation delivery fiber 1112. The position of these lenses is actually adjusted to provide the best imaging of point 1128 onto point 1122 since the achromat 1120 will not be corrected for UV wavelengths.

In this embodiment the reference illumination is derived from the normal red illumination light from the visible light source. Filter 1130 is made of red absorbing glass which strongly attenuates wavelengths UV, blue and green wavelengths. Filter 1130 is mounted on a sliding base 1134, shown in FIG. 11c, and is switched into the optical path electromechanically when autofluorescence imaging is to be used. The shutter in the UV light source is opened at the same time. The tissue will then be illuminated by both the UV and the reference light either simultaneously if a color video endoscope is being used or sequentially if a color wheel video endoscope is being used. Filter 1132 is clear glass which transmits all of the normal visible wavelengths. Filter 1132 is switched in electromechanically when normal illumination is to be used so that the focal point of lens 1116 remains constant.

For the endoscope illumination bundle 1136 to be both UV-transmissive, flexible and long-lasting it must be made of fused silica optical fibers rather than regular glass fibers. The primary optical difference between the two materials, other than transparency, is that fused silica fibers generally have a lower numerical aperture than glass fibers. This means that light is collected and emitted at smaller angles from the axis in fused silica fibers. The illumination bundle bifurcates at point 1138 and exits the optical ports 1140 and 1142 at the distal tip of the endoscope. The lens elements in the ports 1140 and 1142 must also be modified (made more negative) to maintain the same illumination angle for existing, glass fiber based endoscopes.

The video imaging detection system 1144 at the distal tip of the endoscope transmits its signals back down the electrical wires 1146 within the endoscope to the electrical connector 1147 on the connector plug 1104. A mating connector on the adapter box 1100 collects these signals which are transferred across the adapter 1100 to a connector plug 1148 identical to plug 1147 which completes the electrical connections into the video processor. Analysis of the autofluorescence and reference images then proceeds as before.

Figure 12:
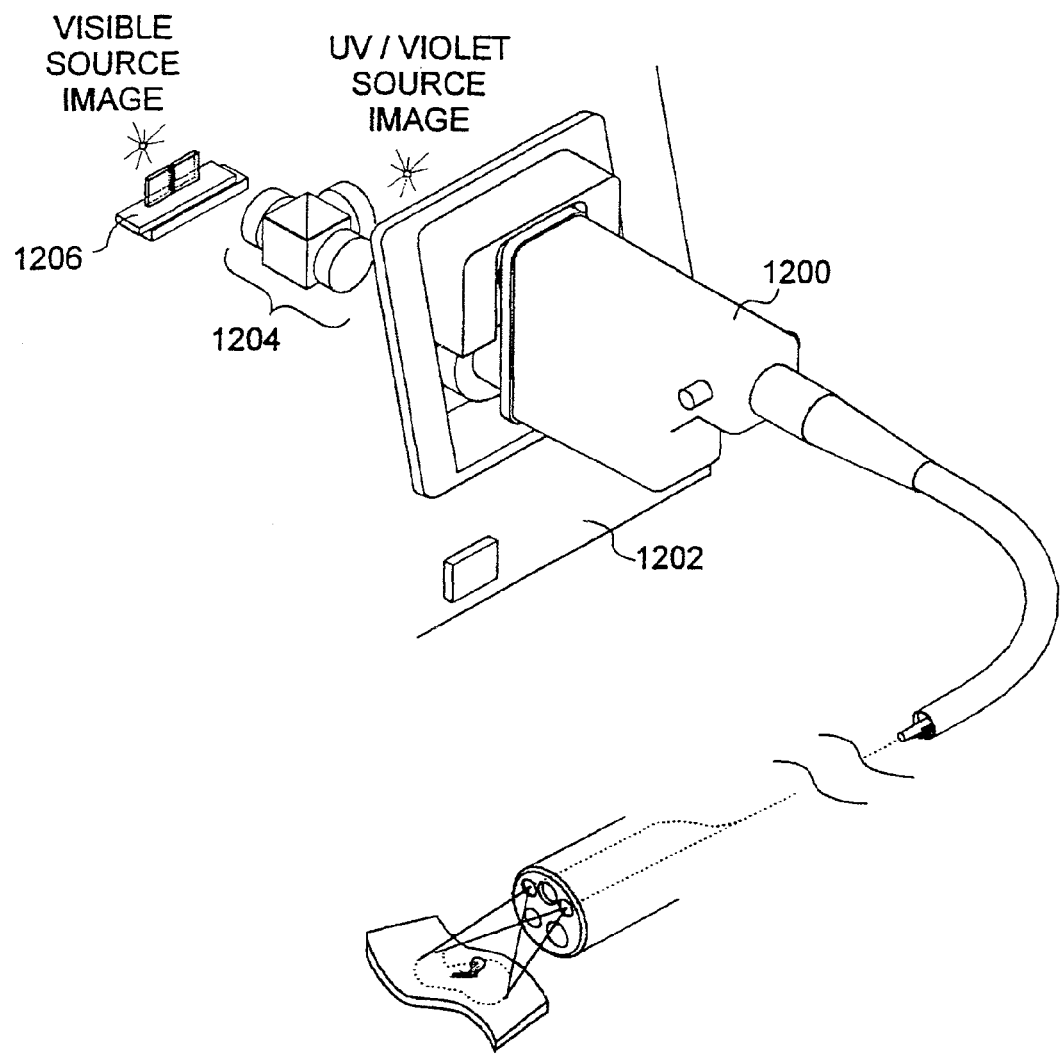
FIG. 12 is a schematic diagram of a preferred embodiment of the imaging system which fully integrates the excitation light source and white light source into an illumination system for an endoscope fitted with UV-transmissive illumination guide.

Once the UV-capable endoscope is available, the excitation source can be built into the endoscope light source and video processor so that the entire autofluorescence imaging capability is included in the endoscope system itself. This preferred embodiment is shown schematically in FIG. 12. The electrical/optical connection plug 1200 is mated directly to the excitation/reference/white light source and video processor 1202. This system operates exactly as the embodiment shown in FIGS. 11a-11d, using a dichroic cube beam combiner system 1204 and a reference light filter system 1206, but without the necessity of an external adapter.

While this invention has been particularly shown and described with references to preferred embodiments thereof, it will be understood by those skilled in the art that various changes in form and details may be made therein without departing from the scope of the invention encompassed by the appended claims.

What is claimed is:

1. A fluorescence imaging endoscope system comprising:
   a diode laser light source for producing excitation light having a wavelength in a range of 380 nm to 420 nm that induces visible autofluorescence in tissue and a second light source for producing a reference light including red, green and blue wavelength bands, the diode laser light source and second light source being operative in response to control signals from a control system;
   an optical combiner that optically couples said excitation light and said reference light onto a common optical path, said excitation light and reference light being coupled into an optical guide that delivers the light to the tissue through an endoscope;
   a single image detector at a distal end of the endoscope that detects an autofluorescence image having blue, green and red light components and a reference image of the tissue; and
   a data processor that processes the autofluorescence image and said reference image to produce a processed output image of the tissue.

2. The system of claim 1 wherein the processed output image comprises a visible light image and a color overlay indicative of a predetermined level of fluorescence intensity.

3. The system of claim 2 wherein the single image detector is a charge coupled device detector.

4. The system of claim 1 wherein the optical guide is a fiberoptic bundle extending through a channel of the endoscope to measure dysplasia in a colon or lung of a subject.

5. The system of claim 1 wherein the detector at a distal end of the endoscope comprises a color charge coupled device.

6. The system of claim 1 wherein the excitation light and the reference light are emitted sequentially such that the image detector comprises a monochromatic image sensor that detects a fluorescence image during a first time period and detects a reflected image during a second time period.

7. The system of claim 1 wherein the excitation light and reference light are actuated in sequence by the control system.

8. The system of claim 1 wherein the optical guide comprises an optical fiber with a distally mounted lens.

9. The system of claim 1 wherein the excitation light has an angular distribution that is the same as an angular distribution of the reference light.

10. The system of claim 1 wherein the single image detector further comprises a pixellated integrated circuit device.

11. The system of claim 1 wherein the single image detector further comprises a CMOS imaging device.

12. The system of claim 1 wherein the diode laser light source comprises a gallium nitride laser diode.

13. The system of claim 12 wherein the gallium nitride laser diode operates at wavelengths in the range of 380 nm to 420 nm.

14. The system of claim 1 wherein the second light source is an arc lamp.

15. The system of claim 1 wherein the second light source is a mercury arc lamp.

16. The system of claim 1 wherein the detected autofluorescence image includes collagen autofluorescence at 450 nm.

17. A fluorescence imaging endoscope system comprising:
a gallium nitride diode laser for producing excitation light having a wavelength in the range of 380 to 420 nm that induces visible autofluorescence in tissue and a second light source for producing a reference light including red, green and blue wavelength bands, the diode laser light source and second light source being operative in response to control signals from a control system;
an optical combiner that optically couples said excitation light and said reference light onto a common optical path, said excitation light and reference light being coupled into an optical fiber delivery system extending through the endoscope system;
a single image detector at a distal end of the endoscope that detects an autofluorescence image having blue, green and red light components and a reference image of the tissue; and
a data processor that processes the autofluorescence image and said reference image to produce a processed output image of the tissue.

18. A fluorescence imaging endoscope system comprising:
a diode laser light source for producing excitation light having a wavelength in the range of 380 to 420 nm that induces visible autofluorescence in tissue and a second light source for producing a color image;
an optical combiner that optically couples said excitation light and said light from the second light source onto a common optical path, said combined light being coupled into an optical guide that delivers the combined light to the tissue through an endoscope;
a single image detector at a distal end of the endoscope that detects an autofluorescence image having blue, green and red light components and a color image of the tissue; and
a data processor that processes the autofluorescence image and said color image to produce a processed output image of the tissue.

19. The system of claim 18, wherein the processed output image comprises a visible light image and a color overlay indicative of a predetermined level of fluorescence intensity.

20. The system of claim 18, wherein the single detector is a charge coupled device detector.

21. The system of claim 18, wherein the single image detector comprises a color charged coupled device.

22. The system of claim 18, wherein the optical guide is a fiberoptic bundle that extends through a channel of the endoscope to measure dysplasia in a colon or lung of a subject.

23. The system of claim 18, wherein the excitation light and red, green, and blue light pulses are emitted sequentially such that the image detector comprises a monochromatic image sensor that detects a fluorescence image during a first time period and detects a reflected color image during a second time period.

24. The system of claim 18, wherein the excitation light and light from the second source are emitted simultaneously such that the respective fluorescence and color images are detected by a color-sensitive image detector.

25. The system of claim 18, wherein the optical guide comprises an optical fiber with a distally mounted lens.

26. The system of claim 18, wherein the excitation light has an angular distribution that is the same as an angular distribution of the light from the second source.

27. The system of claim 18, wherein the single image detector further comprises a pixellated integrated circuit device.

28. The system of claim 18, wherein the single image detector further comprises a CMOS imaging device.

29. The system of claim 18, wherein the diode laser light source comprises a gallium nitride laser diode.

30. The system of claim 18, wherein the second light source is an arc lamp.

31. The system of claim 18, wherein the second light source is a mercury arc lamp.

32. The system of claim 18 wherein the detected autofluorescence image includes collagen autofluorescence at 450 nm.

* * * * *